(12) United States Patent
Dragan et al.

(10) Patent No.: US 8,177,429 B2
(45) Date of Patent: May 15, 2012

(54) FOLDABLE NUCLEAR MEDICINE GANTRY

(75) Inventors: Dumitru Dragan, Fremont, CA (US);
Dean O. Bishop, Livermore, CA (US);
Rizwan S. Hassan, Danville, CA (US);
Jorge I. Zapata, Tracy, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 181 days.

(21) Appl. No.: 12/513,169

(22) PCT Filed: Oct. 31, 2007

(86) PCT No.: PCT/US2007/083081
§ 371 (c)(1),
(2), (4) Date: May 1, 2009

(87) PCT Pub. No.: WO2008/127394
PCT Pub. Date: Oct. 23, 2008

(65) Prior Publication Data
US 2010/0020919 A1    Jan. 28, 2010

Related U.S. Application Data

(60) Provisional application No. 60/866,076, filed on Nov. 16, 2006.

(51) Int. Cl.
*H01J 31/50*    (2006.01)
*G01T 1/166*    (2006.01)

(52) U.S. Cl. .................................. 378/189; 250/363.05
(58) Field of Classification Search ............ 250/363.04, 250/363.05; 378/193–198
See application file for complete search history.

(56) References Cited

U.S. PATENT DOCUMENTS

| | | | |
|---|---|---|---|
| 5,365,069 A | 11/1994 | Eisen et al. | |
| 5,499,284 A * | 3/1996 | Pellegrino et al. | 378/198 |
| 5,594,251 A | 1/1997 | Fleury et al. | |
| 6,160,258 A | 12/2000 | Maor | |
| 6,242,742 B1 | 6/2001 | Geay et al. | |
| 2005/0205795 A1 | 9/2005 | Blevis et al. | |
| 2006/0078091 A1* | 4/2006 | Lasiuk et al. | 378/198 |
| 2007/0246656 A1* | 10/2007 | Blevis et al. | 250/363.05 |

FOREIGN PATENT DOCUMENTS

| | | |
|---|---|---|
| EP | 0387956 A1 | 9/1990 |
| EP | 1420269 A1 | 5/2004 |

* cited by examiner

*Primary Examiner* — Hoon Song

(57) ABSTRACT

In accordance with one aspect, imaging system (10, 190) includes a plurality of detector heads (12, 14, 80, 100, 202) and a frame (20) on which the plurality of detector heads are mounted. The frame is configurable in (i) an operational configuration in which the detector heads are arranged to be manipulated by the frame to acquire imaging data, and (ii) a shipping configuration in which the detector heads remain mounted on the frame and the imaging system is reduced in size along at least one dimension compared with the operational configuration.

27 Claims, 15 Drawing Sheets

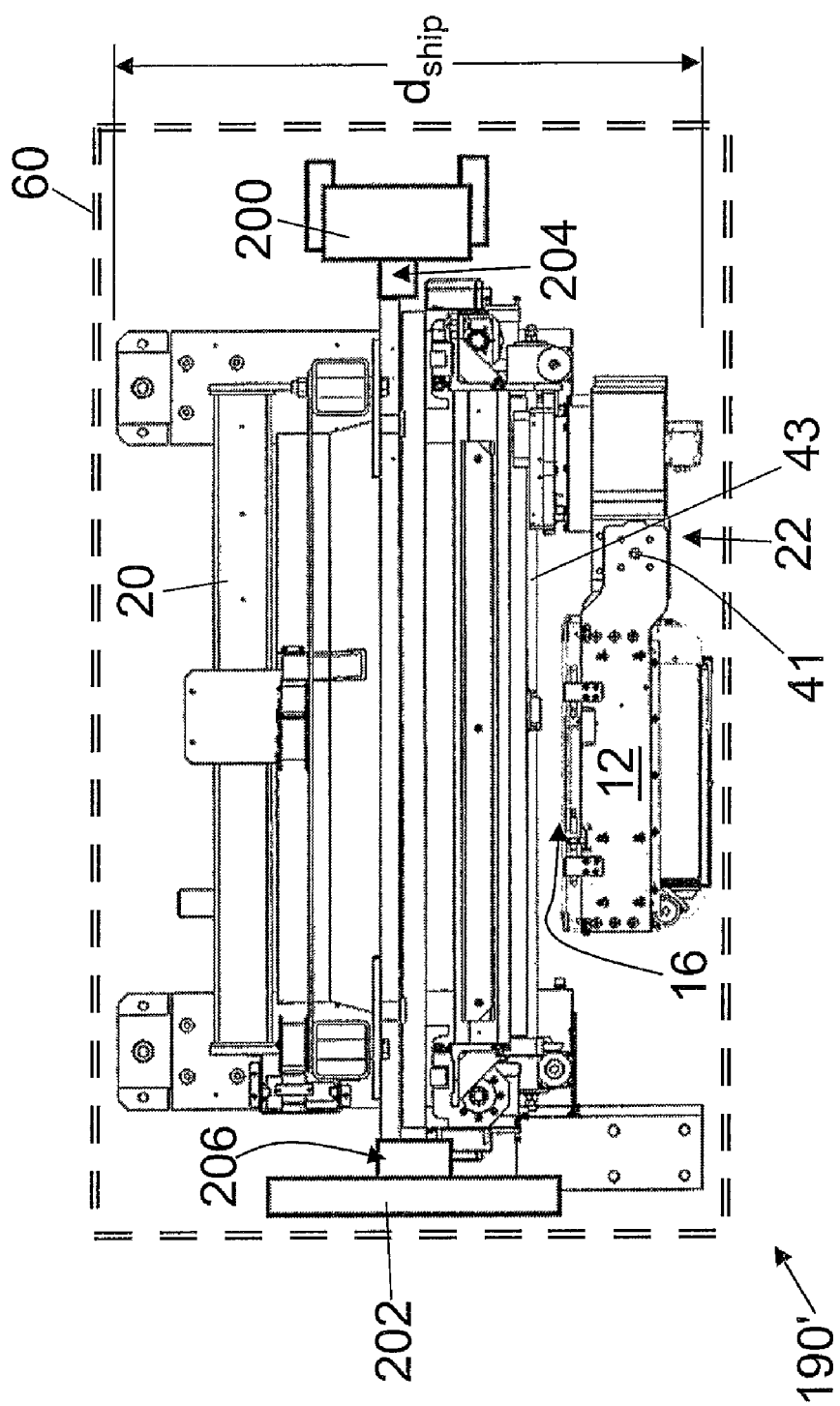

FOLDABLE NUCLEAR MEDICINE GANTRY

CROSS REFERENCE TO RELATED APPLICATIONS

This application claims the benefit of U.S. provisional application Ser. No. 60/866,076 filed Nov. 16, 2006, which is incorporated herein by reference.

The following relates to medical imaging systems. It especially relates to gamma cameras including two, three, four, or more radiation detector heads, and is described with particular reference thereto. The following relates more generally to medical imaging systems of various types that use extended mechanically manipulated detector heads and/or radiation sources.

A typical commercial gamma camera includes a mechanical frame configured to support and manipulate two, three, four, or more radiation detector heads. Each radiation detector head is itself a massive and complex unit, typically including an array of radiation detectors, a heavy collimator made of lead or another heavy metal material, and lead or other radiation shielding encasement. In a usual manufacturing and product delivery workflow, the components are manufactured and assembled at a factory for alignment and testing. Alignment marks are made on adjustable mechanical alignment components of the frame and/or on the detector heads during such factory testing. Once testing is complete, the massive assembly is disassembled so that the detector heads are shipped separately from the robotic frame. At a hospital or other shipping destination, the shipped components are collected and reassembled. The alignment marks made at the factory are useful in reassembling the gamma camera; however, re-testing at the destination is done to ensure proper alignment.

Modem hospitals and other medical facilities in the United States typically have doorways of 40-inches (100 cm) wide, while in Europe 36-inch (90 cm) doorways are sometimes used. The assembled gamma camera is too large to fit through such doors. Accordingly, the conventional process of disassembly, shipping, and reassembly at the destination is required in order to deliver the gamma camera components to a typical medical imaging room destination at a hospital or other destination facility.

However, this approach of disassembly and separate shipping of the frame and individual radiation detector heads has disadvantages. The manual disassembly and reassembly processing provides opportunities for human error that can delay installation or damage gamma camera components. The technicians at the delivery site must be sufficiently skilled to perform the reassembly and testing on-site, including such complex operations as reconnecting the numerous electrical cabling connections, and mechanically securing together each radiation detector head with its mating manipulation robotics. These mechanical connections are complex, being configured to provide several degrees of mechanical freedom for manipulating each detector head. For example, some commercial gamma cameras are six-axis gantry systems with two radiation detectors and two mating robotic arms. More recently developed commercial gamma cameras include more radiation detector heads and a concomitant increase in the complexity of disassembly and reassembly. Moreover, the relative positions of detector heads must be established at the destination so that, for example, when the operator sets the detector heads to face each other at 180° azimuthally separated positions, the detector heads are precisely positioned opposite each other. While the alignment marks made at the factory facilitate this process, the disassembly and reassembly can introduce misalignment that can only be corrected by retesting and realignment of the reassembled system at the destination site.

Shipment in the disassembled condition also increases shipping costs. Each component, including the robotic frame and each individual radiation detector head, must be separately packaged and shipped, which increases shipping material costs. Additionally, disassembled smaller components such as bolts and so forth must also be packaged and shipped, which further increases shipping cost. Such smaller components are prone to being lost during disassembly, during shipment, or at the delivery site, which can introduce delays and additional expense in the gamma camera installation.

The following provides a new and improved apparatuses and methods which overcome the above-referenced problems and others.

In accordance with one aspect, imaging system is disclosed, including a plurality of detector heads and a frame on which the plurality of detector heads are mounted. The frame is configurable in (i) an operational configuration in which the detector heads are arranged to be manipulated by the frame to acquire imaging data, and (ii) a shipping configuration in which the detector heads remain mounted on the frame and the imaging system is reduced in size along at least one dimension compared with the operational configuration.

In accordance with another aspect, a shipping package is disclosed, including the imaging system as set forth in the preceding paragraph configured in the shipping configuration in which the detector heads remain mounted on the frame, and packaging material containing or covering at least a portion of the imaging system.

In accordance with another aspect, and imaging system is disclosed, including: a plurality of detector heads; a frame; and manipulators mechanically and electrically connecting the detector heads with the frame. The manipulators include a plurality of operational degrees of mechanical freedom usable in operating the imaging system to acquire imaging data and at least one additional degree of mechanical freedom usable to selectively arrange the imaging system in a shipping configuration in which the plurality of detector heads are mechanically connected with the frame and the imaging system has a reduced size in at least one dimension compared with a size compared with a size of the imaging system during imaging data acquisition.

In accordance with another aspect, a delivery method is disclosed for delivering an imaging system including at least a frame and a plurality of detector heads. At a first location, a plurality of detector heads are mounted on a frame via manipulators configured to provide a plurality of operational degrees of mechanical freedom for manipulating the detector heads during imaging data acquisition. At the first location, the detector heads are electrically connected with the frame. At the first location, the detector heads are placed in a shipping configuration in which the plurality of detector heads remain mounted and a size of the imaging system is reduced compared with a size of the imaging system during imaging data acquisition. The imaging system is shipped in the shipping configuration from the first location to a second location different from the first location.

In accordance with another aspect, a shipping package is disclosed, including: an imaging system and packaging material. The imaging system includes a plurality of detector heads mechanically connected with a frame configured in a reduced size configuration that is smaller along at least one dimension than an operational configuration of said imaging system. The packaging material contains or covers at least a portion of the imaging system.

In accordance with another aspect, an imaging system is disclosed, including: a frame; at least one imaging component mounted cantilevered from the frame; and a means for enabling the at least one imaging component to be tipped toward the frame to a shipping configuration of reduced width.

In accordance with another aspect, an imaging system is disclosed, including a frame, an imaging component, and an arm having first and second ends. The first end has a pivot connection with the frame. The second end is connected with the imaging component. The has an operational position rotated about the pivot connection to position the imaging component relatively further from the frame for imaging, and has a shipping position rotated about the pivot connection to position the imaging component relatively closer to the frame for shipping.

One advantage is reduced assembly of a shipped gamma camera at the hospital or other destination.

Another advantage is reduced likelihood of introducing detector head misalignment during shipment and setup of a gamma camera.

Another advantage is reduced likelihood of damaging a shipped gamma camera during assembly at a hospital or other destination.

Another advantage is reduced likelihood of losing loose components during shipment and setup of a gamma camera.

Another advantage is reduced shipping costs for shipping a gamma camera.

Still further advantages of the present invention will be appreciated to those of ordinary skill in the art upon reading and understand the following detailed description.

The invention may take folds in various components and arrangements of components, and in various steps and arrangements of steps. The drawings are only for purposes of illustrating the preferred embodiments and are not to be construed as limiting the invention.

FIGS. 1, 2, and 3 show front, side, and top views, respectively, of an illustrative gamma camera in an operational configuration.

FIGS. 4, 5, and 6 show front, side, and top views, respectively, of the illustrative gamma camera of FIGS. 1-3, but in a shipping configuration.

FIG. 7 diagrammatically shows a suitable manufacturing, shipping, and delivery system for delivering the gamma camera of FIGS. 1-6 from a manufacturing site to a hospital or other destination site.

Figure 10:
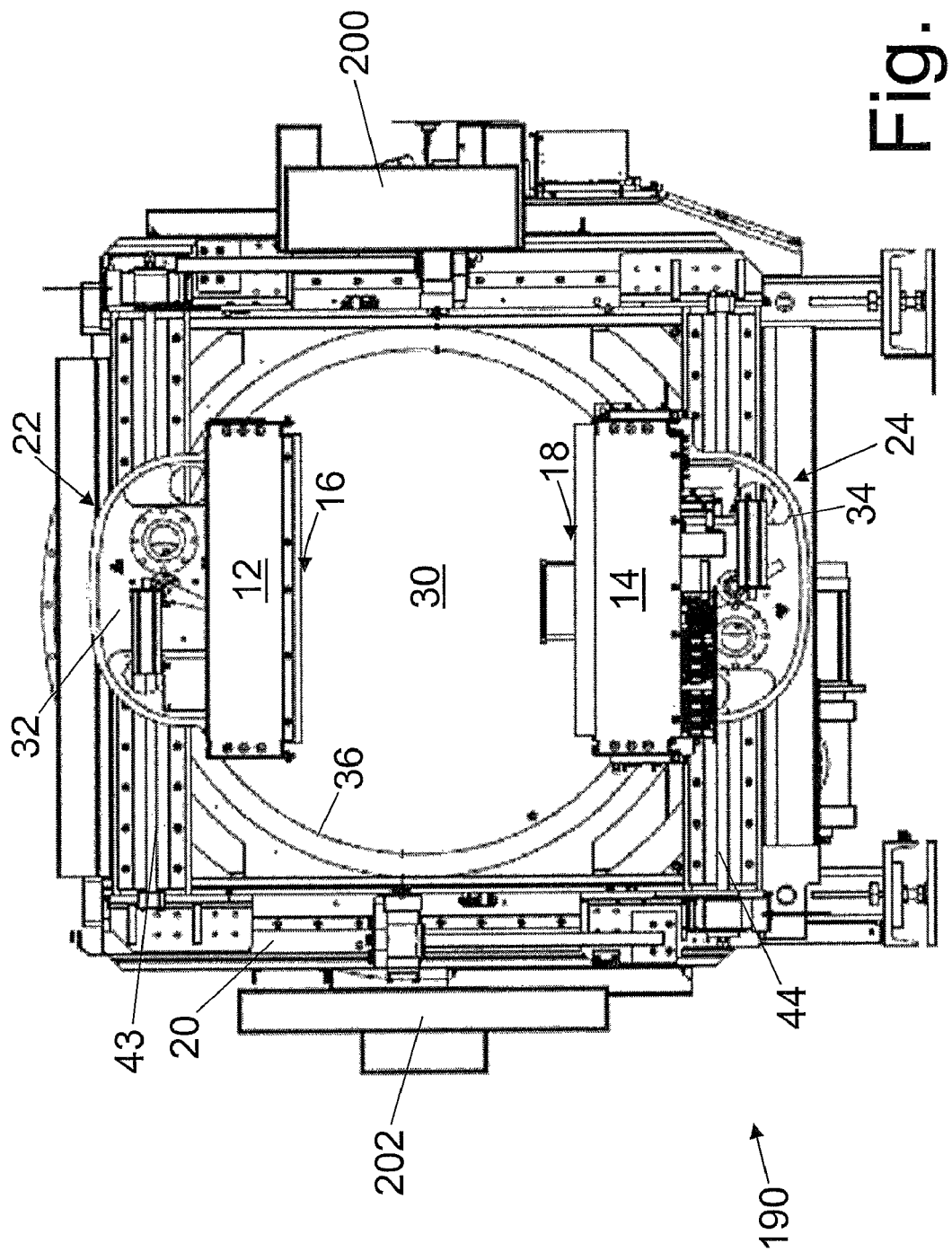
Figure 11:
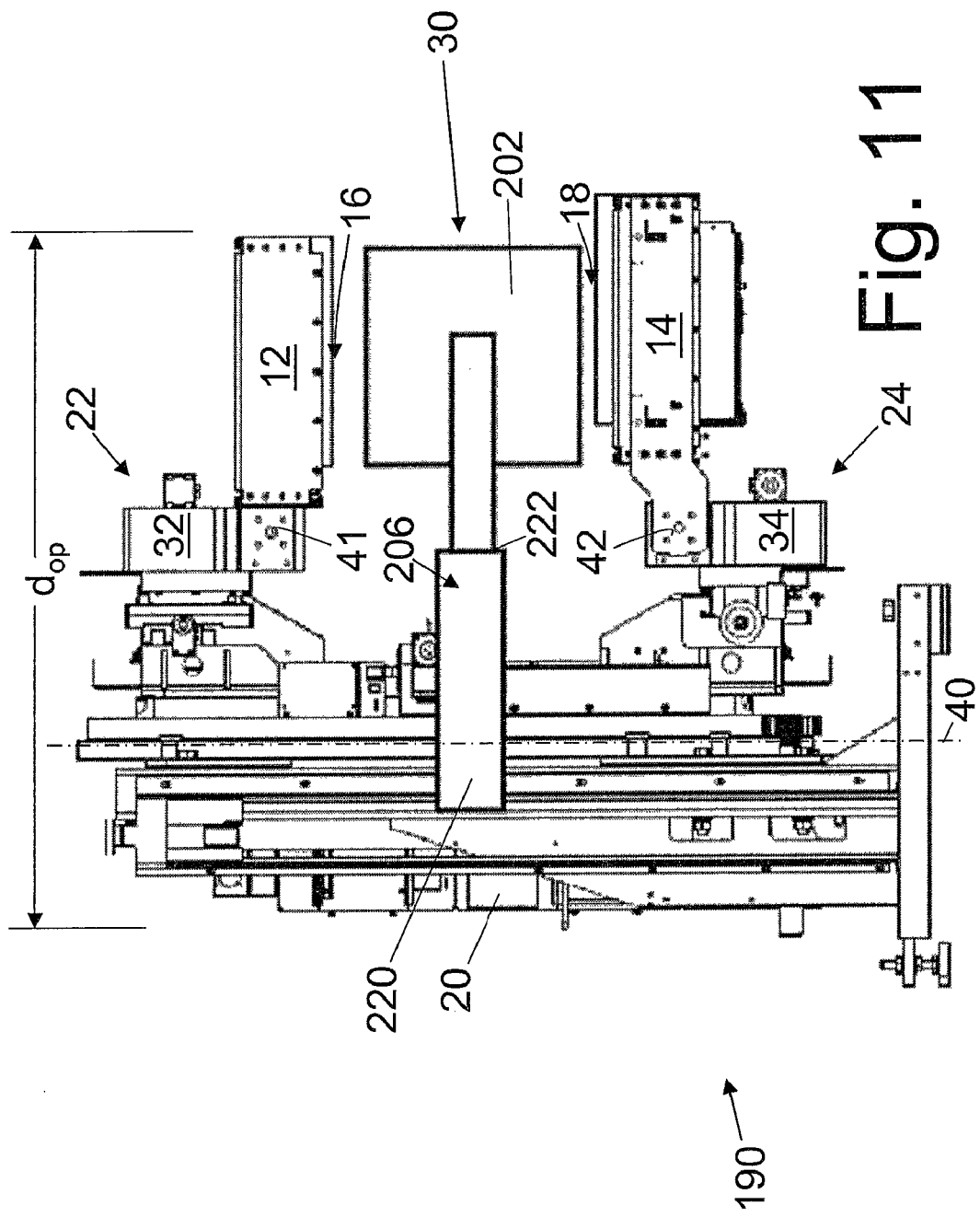
Figure 12:
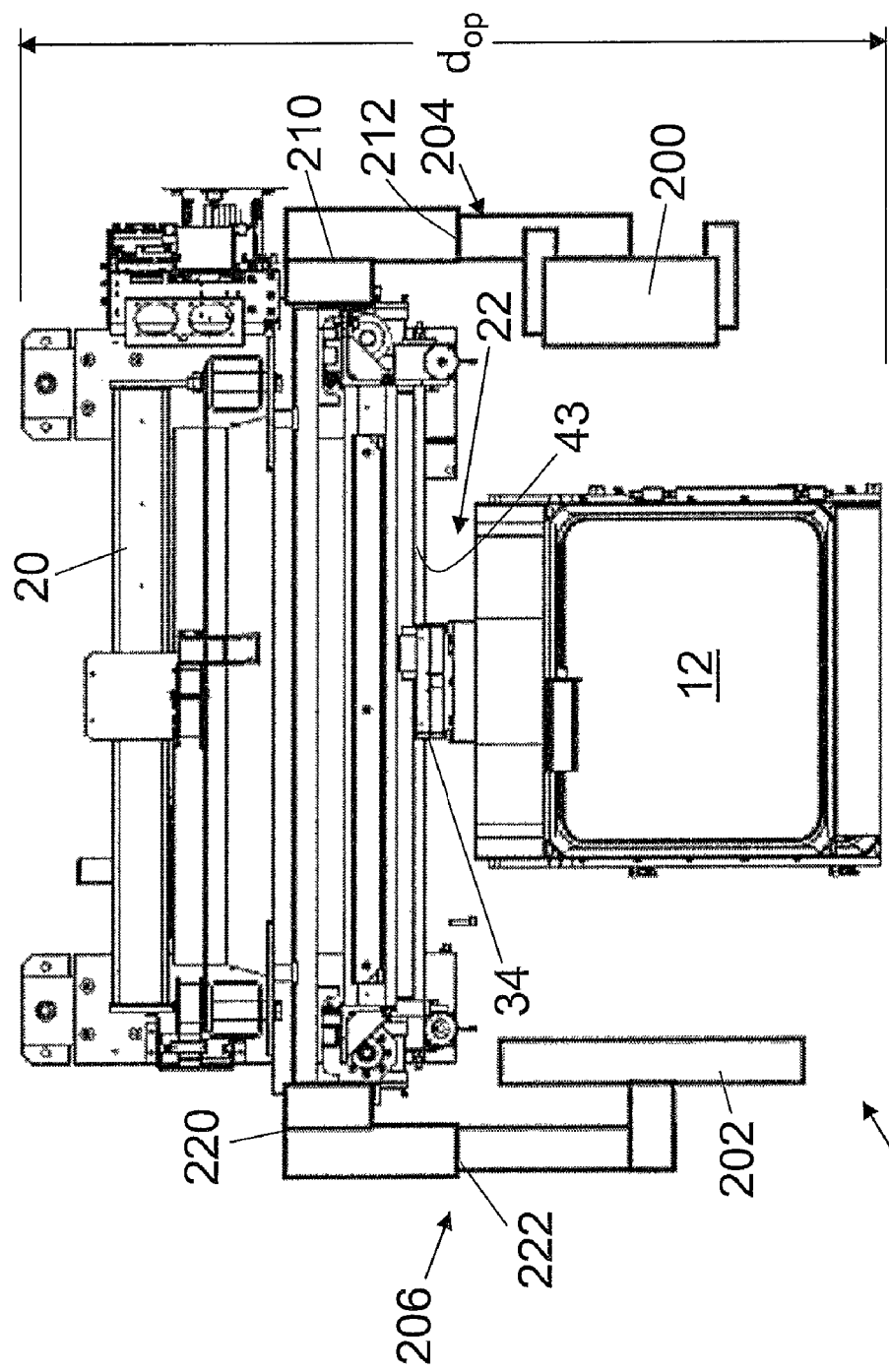

FIGS. 10, 11, and 12 show front, side, and top views, respectively, of an illustrative imaging system in an operational configuration.

Figure 9:
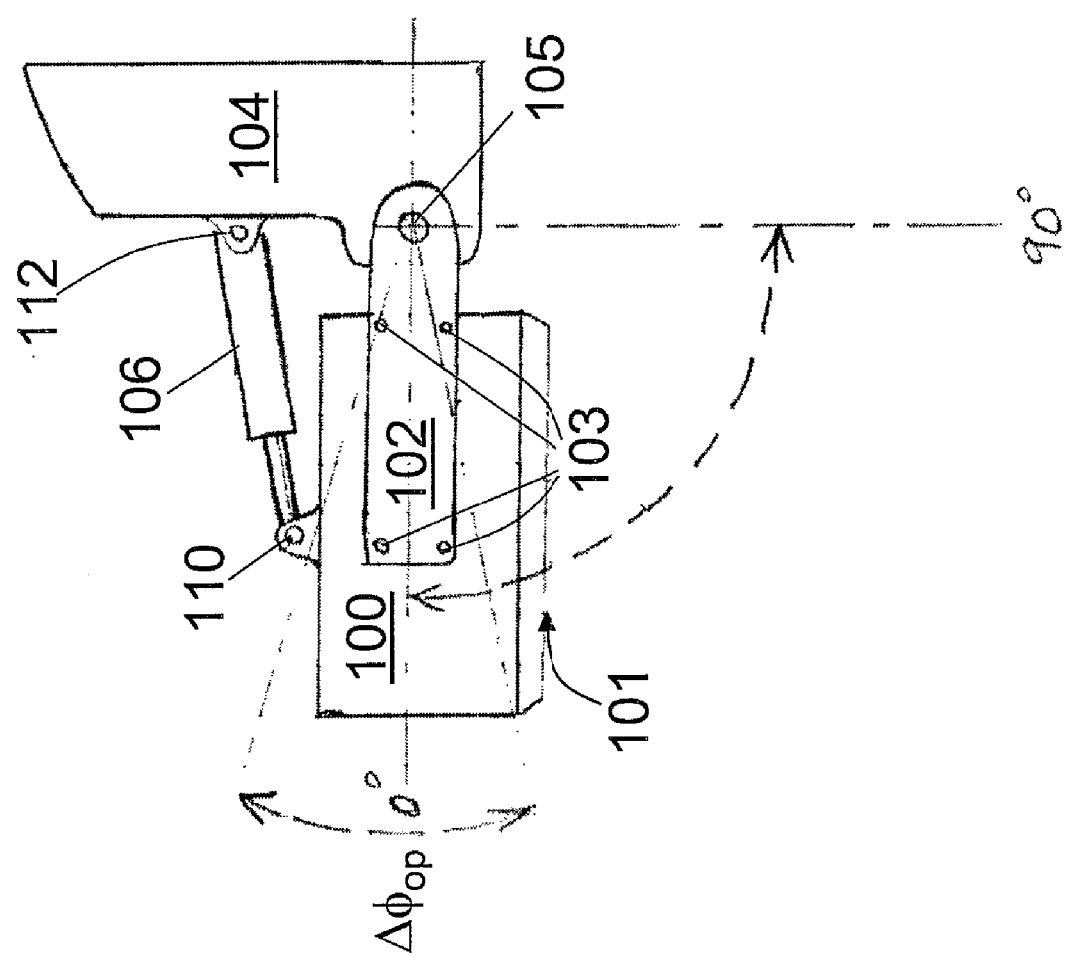
FIG. 9 shows another illustrative arrangement for reconfiguration of a detector head between operational and shipping configurations.
Figure 13:
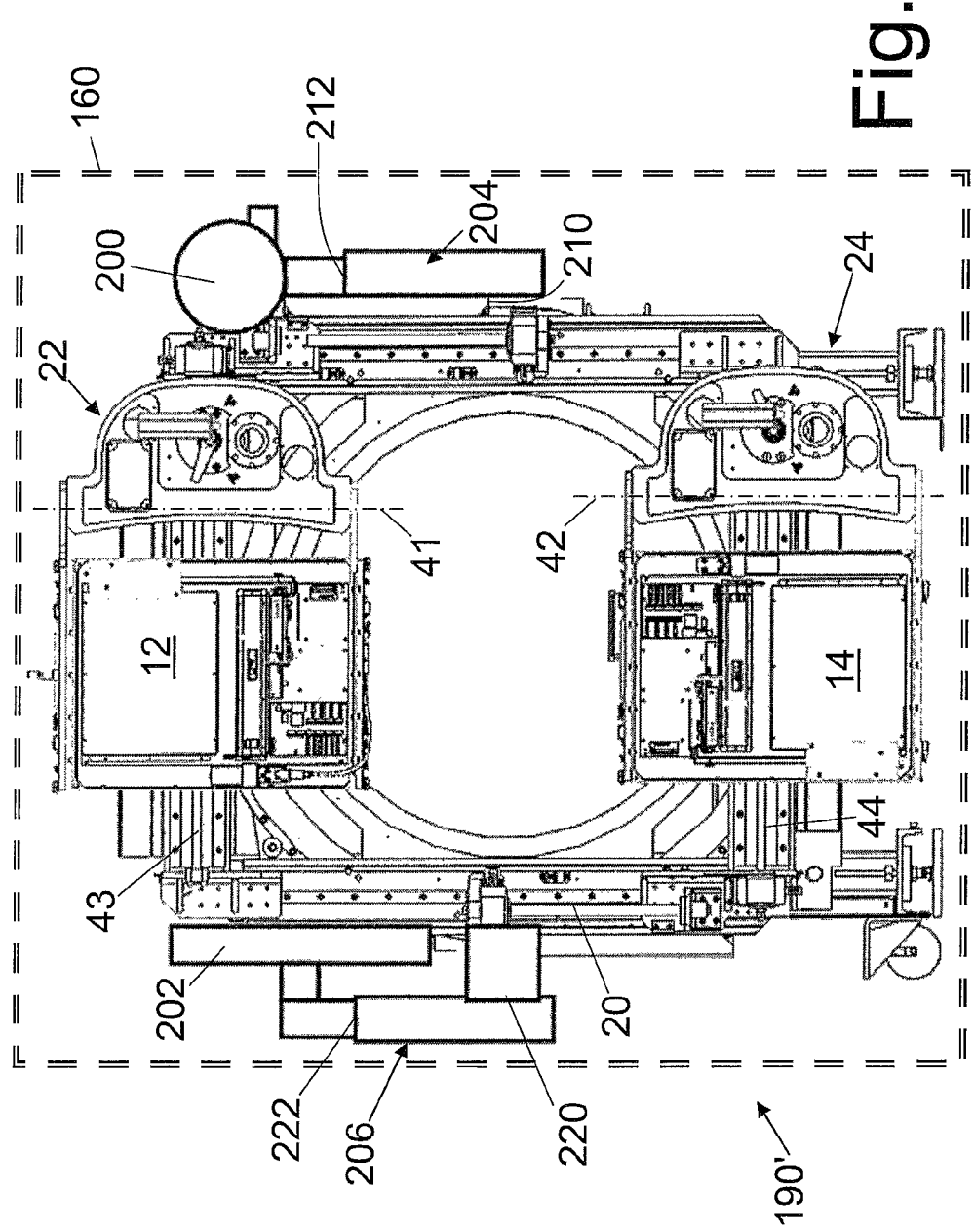
Figure 14:
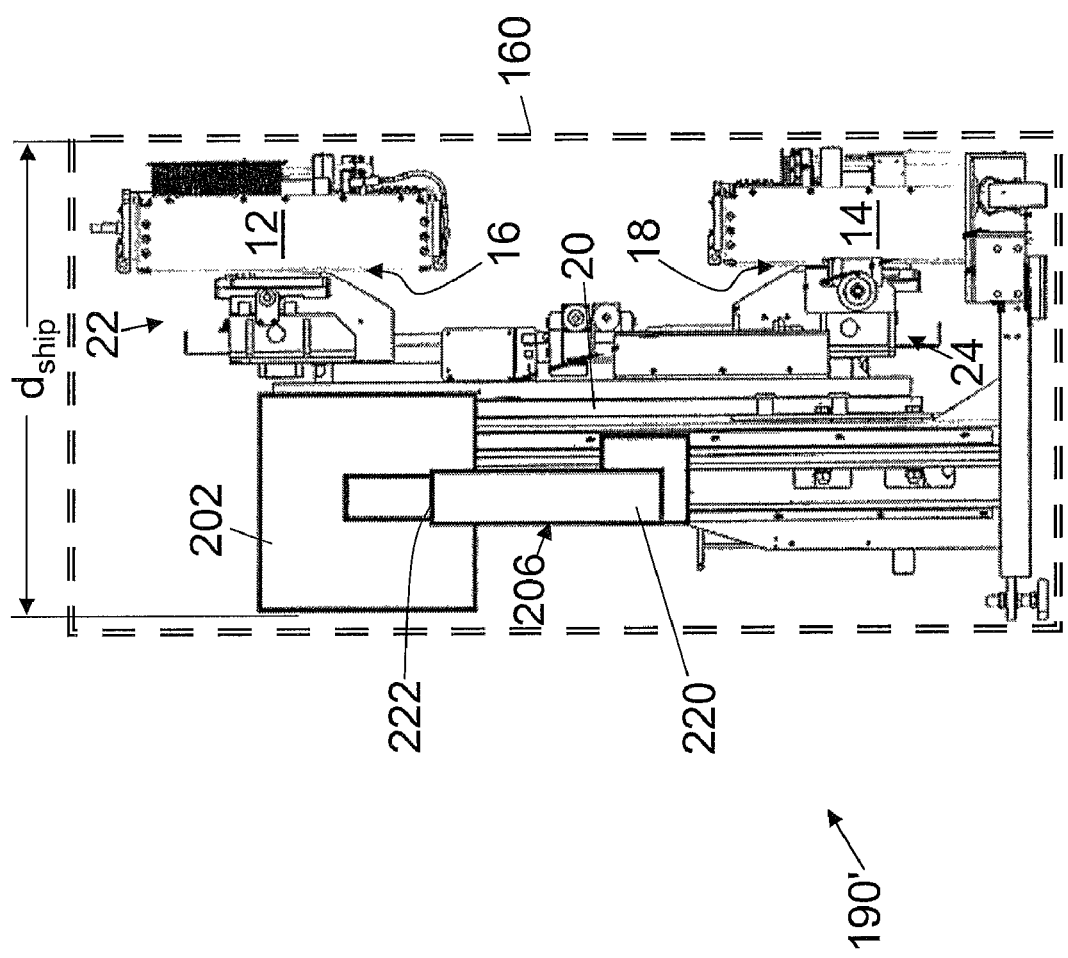

FIGS. 13, 14, and 15 show front, side, and top views, respectively, of the illustrative imaging system of FIGS. 9-11, but in a shipping configuration.

Figure 1:
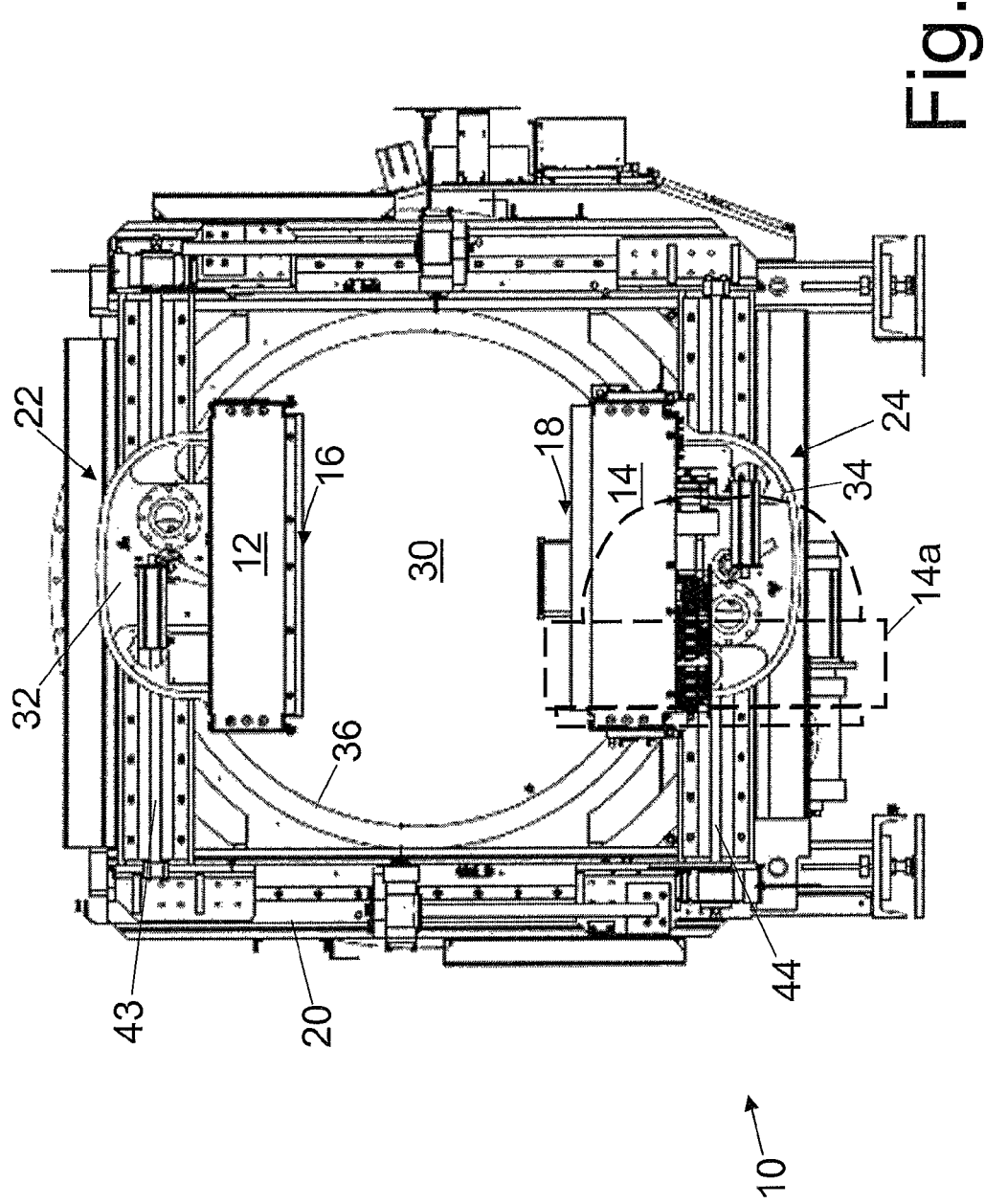
Figure 2:
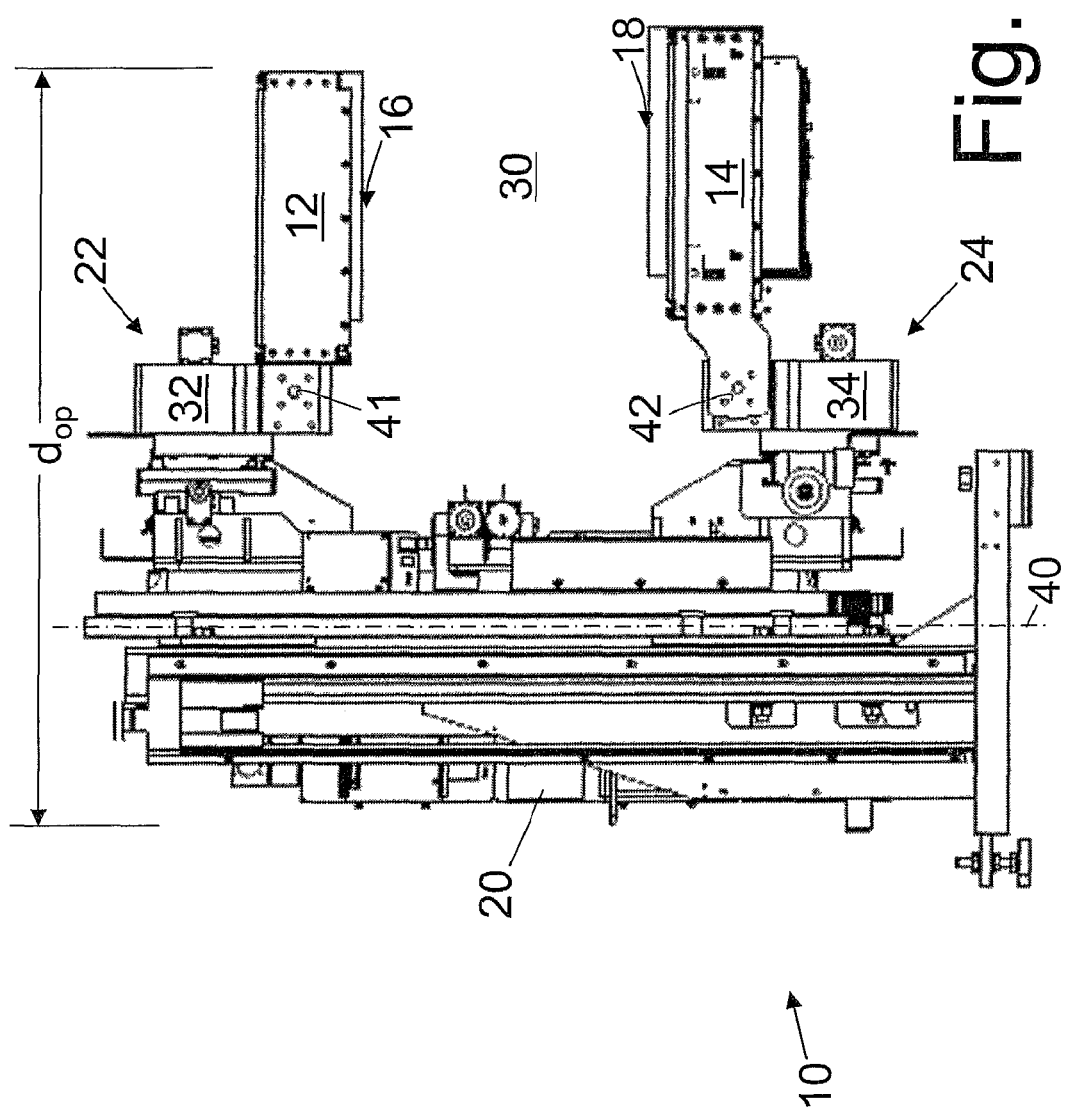
Figure 3:
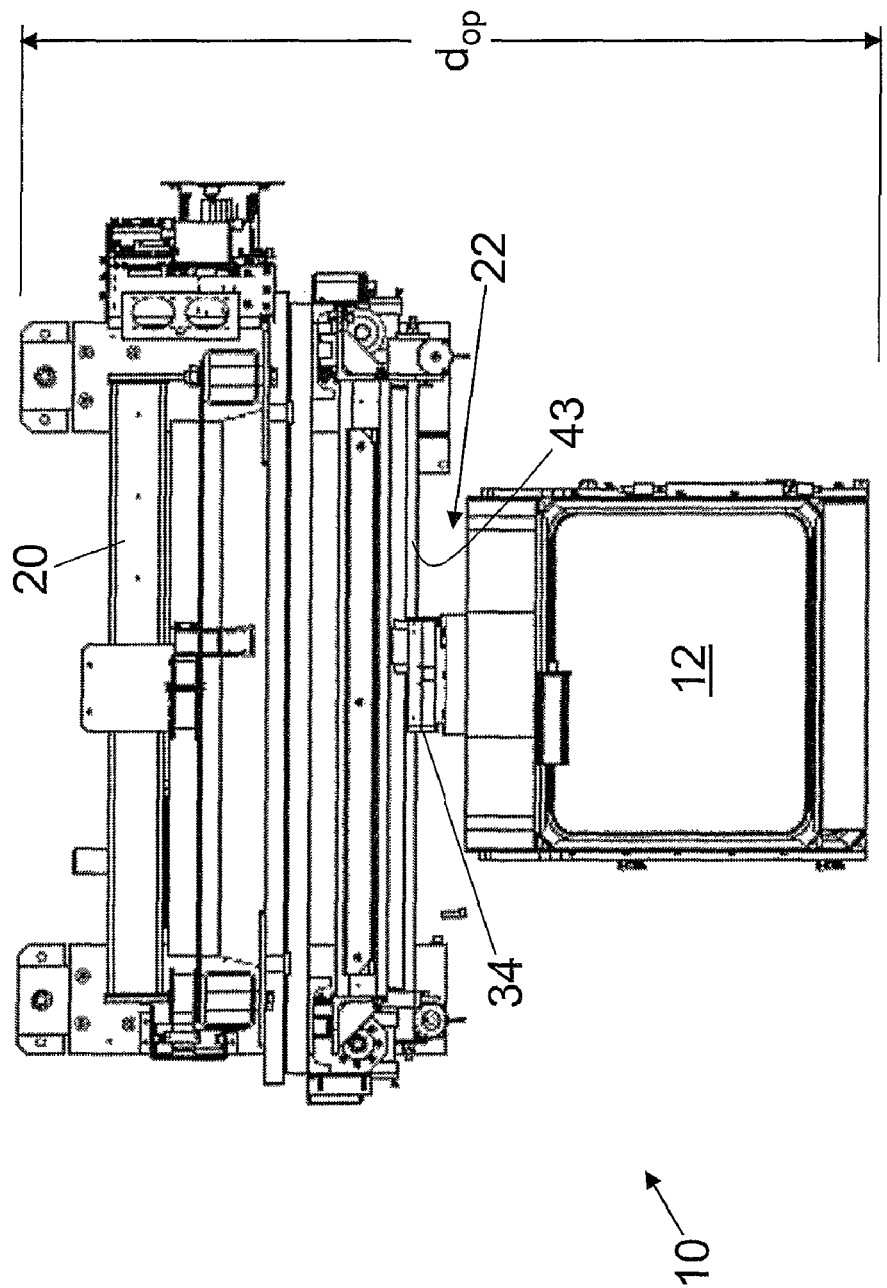

FIGS. 1, 2, and 3 show front, side, and top views, respectively, of an illustrative imaging system, namely an illustrative gamma camera 10, having two detector heads 12, 14 each including a respective radiation-sensitive face 16, 18. The two-head gamma camera 10 is an illustrative example, and it is to be appreciated that the apparatuses and methods disclosed herein for facilitating shipment and reassembly of the imaging system at the destination location are applicable to gamma cameras, CT/SPECT systems, PET/SPECT systems, and other imaging systems that include detector heads mounted on mechanical frames. Moreover, the apparatuses and methods disclosed herein for facilitating shipment and reassembly of the imaging system at the destination location are applicable to gamma cameras or other imaging systems having two detector heads, three detector heads, four detector heads, or more detector heads.

The detector heads 12, 14 are mounted on a frame 20 that includes manipulators 22, 24 for mechanically manipulating the respective detector heads 12, 14. In the illustrated embodiment, the frame 20 defines a bore through which a patient can be moved in a prone position. In the operational configuration shown in FIGS. 1-3, the manipulators 22, 24 position the detector heads such that their respective radiation-sensitive faces 16, 18 face the subject to be imaged. In the operational configuration shown in FIGS. 1-3, the radiation-sensitive faces 16, 18 view a central examination region 30. Such a position is suitable, for example, to perform tomographic imaging of a patient lying on a couch, bed, or pallet (not shown) in the examination region 30 between the radiation-sensitive faces 16, 18. In other operational configurations other orientations of the detector heads 12, 14 may be used. For example, FIG. 1 shows in phantom another possible position 14a of the detector head 14 that is suitable for acquiring planar imaging data from a standing or sitting patient. The illustrated manipulators 22, 24 include respective detector-rotate housings or assemblies 32, 34. For example, the detector-rotate housing or assembly 34 enables rotation of the detector head 14 into the position 14a illustrated in phantom in FIG. 1. Additional operational degrees of freedom provided by the mechanical frame 20, including the exemplary manipulators 22, 24 and other mechanisms, enable revolving the detector heads 12, 14 around the bore along a circular gantry path 36 (best seen, and labeled, in the front view of FIG. 1).

Typically, the operational degrees of freedom do not include a tilt mechanism or other degree of freedom that enables tilting of the detector head to a position more parallel with a principal plane 40 (drawn and labeled in the side view of FIG. 2) of the frame 20. Rather, the radiation-sensitive faces 16, 18 of the detector heads 12, 14 are arranged generally transverse to the principal plane 40 when the gamma camera 10 is in the operational configuration as shown in FIGS. 1-3. As a result, the detector heads 12, 14 protrude relatively far outward away from the main body of the frame 20. Although this arrangement is good for imaging, it is bad for shipping, because it results in a relatively large size $d_{op}$ of the gamma camera 10 along the direction in which the detector heads 12, 14 protrude. The size $d_{op}$ is larger than the typical 36-inch (90 cm) width of a typical European hospital doorway, and is larger than the typical 40-inch (100 cm) width of a typical U.S. hospital doorway.

Figure 4:
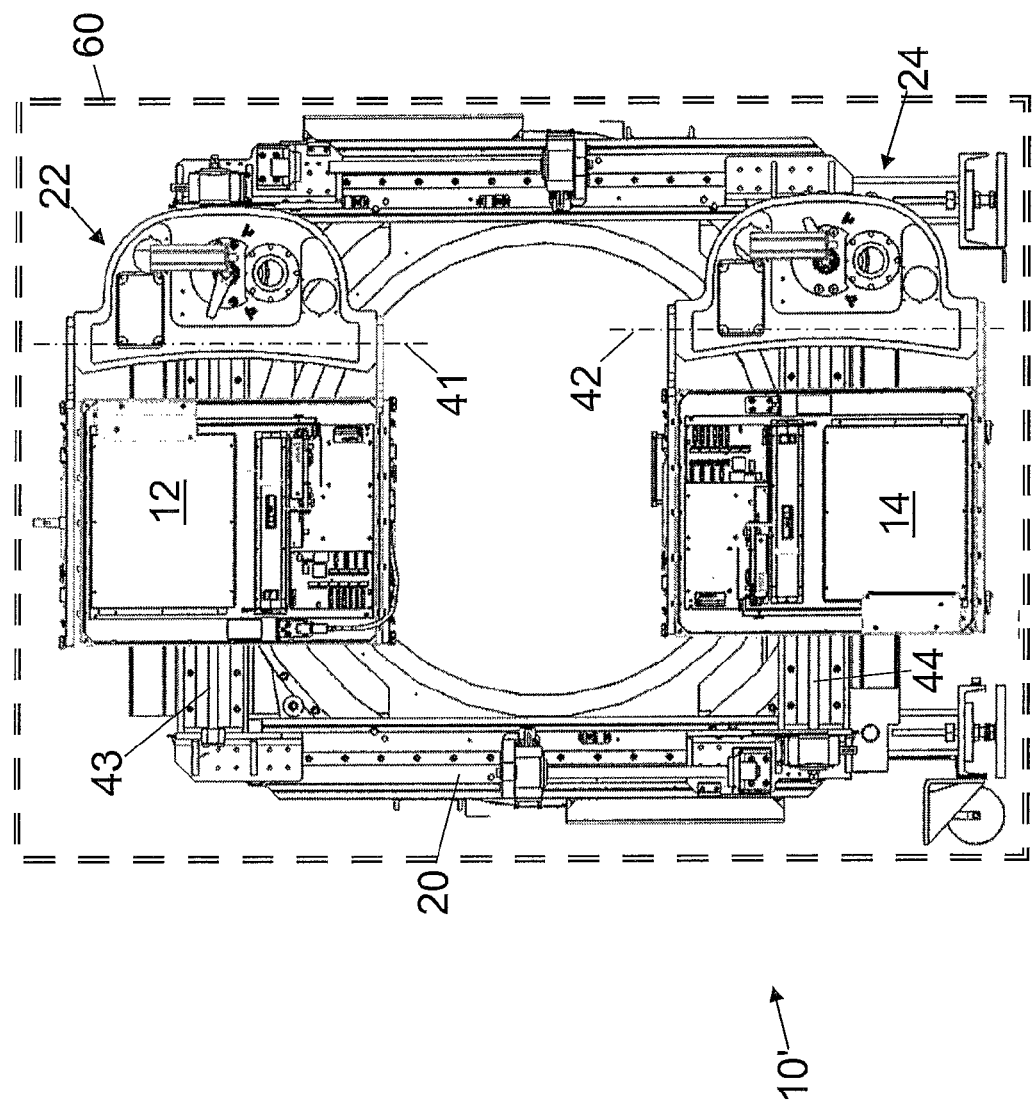
Figure 5:
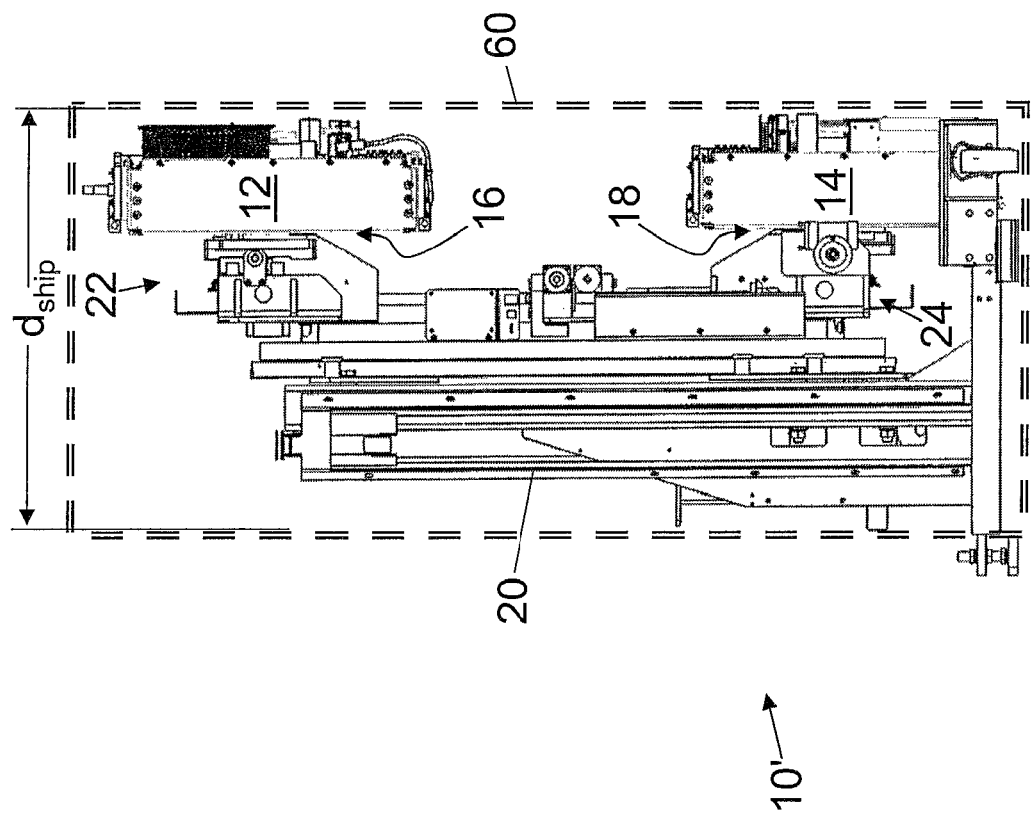
Figure 6:
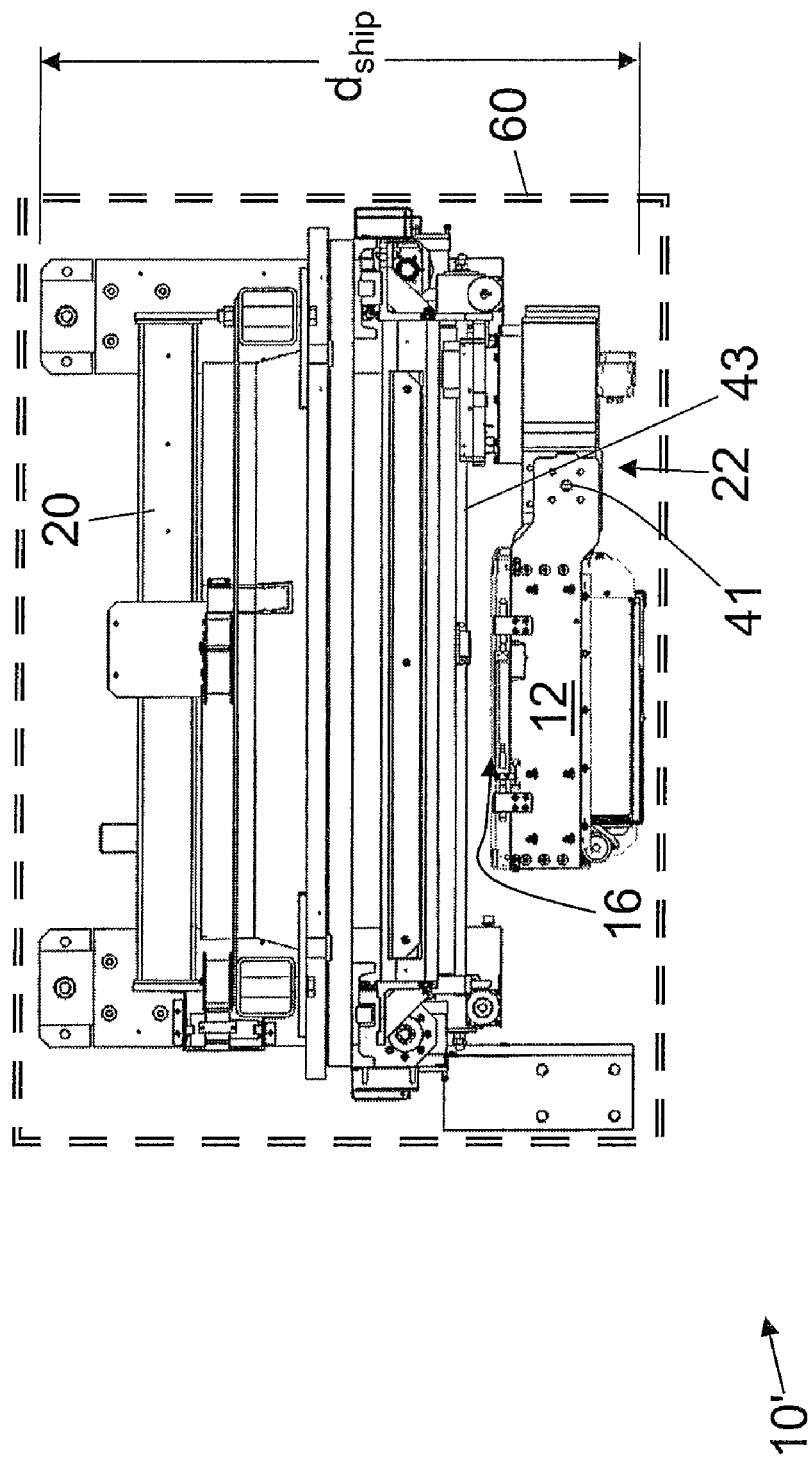

With reference now to FIG. 4-6, the frame 20 of the gamma camera 10 includes at least one additional degree of freedom that is not used in imaging, but which is used for reconfiguring the gamma camera 10 into a more compact shipping configuration in which size of the gamma camera 10 is reduced to a smaller value $d_{ship}$ as indicated in FIGS. 5 and 6. This is accomplished by providing a tilt or pivot joints 41, 42 (labeled in the unfolded or operational configuration in FIG. 2 and in the folded or shipping configuration in FIGS. 4 and 6) that enables the detector heads 12, 14 to pivot or fold such that the radiation-sensitive faces 16, 18 are arranged parallel with and facing the principal plane 40 of the frame 20. In the illustrated embodiment, the folding of the detector heads 12, 14 is done in cooperation with the operational detector head rotate degrees of freedom and the operational revolution degree of freedom 36 provided by the detector-rotate housings 32, 34 of the manipulators 22, 24 to place the detector heads 12, 14 at top and bottom of the frame 20, and to rotate the detector heads 12, 14 so that they do not collide when folded toward the frame 20. In the illustrated embodiment, an additional degree of freedom is provided by respective translational mechanisms 43, 44 (labeled in the unfolded or operational configuration in FIG. 1 and in the folded or shipping configuration in FIG. 4), which are not used in imaging, to approximately center the folded detector heads 12, 14 at the top and bottom of the frame 20.

Figure 7:
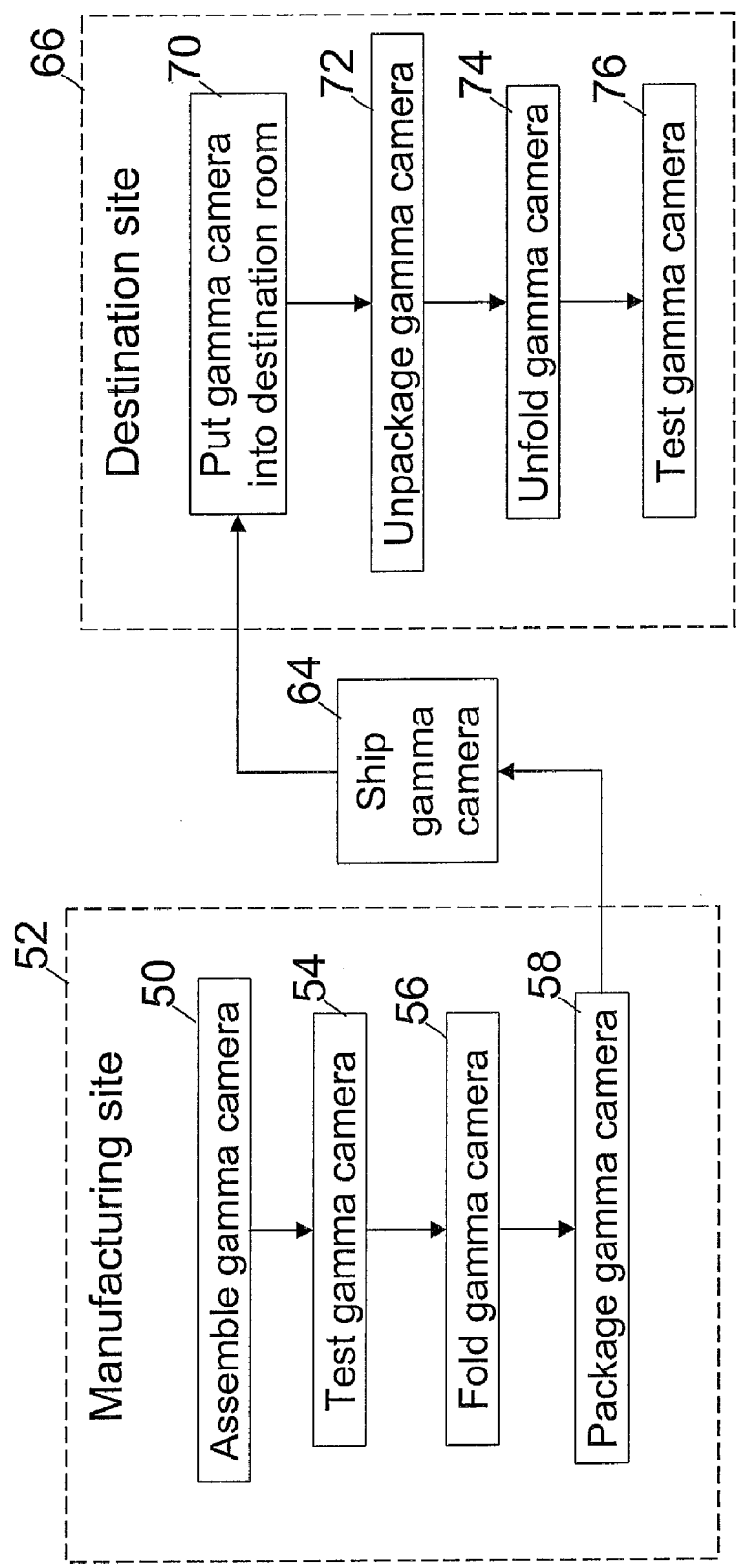

With continuing reference to FIGS. 4-6 and with further reference to FIG. 7, the gamma camera 10 is initially assembled 50 at a factory or other manufacturing site 52 and tested 54 at the manufacturing site 52, as shown, or at another testing facility. The assembly 50 includes mechanically mounting the detector heads 10, 12 on the manipulators 22, 24 of the frame 20, and electrically connecting the detector heads 12, 14 with the manipulators of the frame 20. After the testing 54, the gamma camera 10 is not disassembled, but rather the gamma camera 10 is folded 56 using frame 20 including the manipulators 22, 24. The folding is optionally fully automated and performed wholly by robotic control, or optionally includes some manual operations such as removing locking bolts or the like, manually folding the unlocked detector heads along the pivot joints 41, 42 or so forth. The folded detector heads 12, 14 are suitably held in the folded position frictionally, or by latches, restraining bands, locking bolts or other fasteners, or so forth. In some embodiments, the detector heads 12, 14 remain electrically connected in the folded configuration of FIGS. 4-6. On other embodiments, the detector heads 12, 14 are partially or wholly electrically disconnected.

As used herein, the detector heads 12, 14 are considered to remain electrically connected if they remain substantially electrically connected, even if a small portion of the electrical connections are disconnected when the gamma camera 10 is placed in the folded configuration. For example, it is contemplated to keep the detector heads 12, 14 electrically connected but to disconnect one or a few connections such as to attach a protective electrical termination on certain voltage-sensitive terminals of the detector heads 12, 14, or to disconnect the main power cable to enable shipping, or so forth. If a few connections are disconnected in the folded or shipping configuration, the few disconnected connectors are optionally keyed by connector shape, keying slots, or the like to ensure that these few electrical connections can be re-established in an error-free manner at the destination.

With continuing reference to FIGS. 4-7, once the gamma camera 10 is placed in the folded configuration, it is suitably packaged 58, for example by substantially surrounding the gamma camera 10 in the folded configuration with packaging material 60 as shown diagrammatically in phantom in FIGS. 4-6. The gamma camera in the folded and packaged configuration is then shipped 64 from the factory or other manufacturing site 52 to a hospital, laboratory, or other destination site 66. At the destination site 66, the gamma camera 10 is placed into a destination room in a delivery operation 70, which may involve passing the gamma camera 10 in the folded and packaged configuration through doorways of 40-inch width (as is typical in the United States), or through doorways of 36-inch (90 cm) width (as is typical in Europe). The folded configuration of the gamma camera 10 is such that the dimension $d_{ship}$ is small enough to pass through such doorways. It is contemplated for the gamma camera intended for shipment in the United States to have a width of, for example, 38-inches (96 cm), which is sufficient to pass through typical U.S. hospital doorways. It is further contemplated for the dimension $d_{ship}$ to be greater than 40-inches if the destination site 66 has suitably larger doors.

Once delivered to the destination room, which is typically the room in which the gamma camera 10 is to be operated, the packaging material 60 is removed in an unpackaging operation 72. In some embodiments, the delivery operation 70 and the unpackaging operation 72 may be swapped, i.e., the packaging may be removed wholly or in pail at a hospital unloading dock or other outer region of the destination site 66 before the delivery 70 of the gamma camera 10 in the folded configuration to the destination room. This might be done, for example, to minimize the dimension $d_{ship}$ if the doors, hallways or other standard building structures en-route to the destination room might create a tight fit with the added size of the packaging material 60. In other situations, it may be desirable to leave the packaging material in place until the system reaches the destination room, so as to protect the system as in traverses through the building structures. Once the gamma camera 10 is in the destination room and the packaging material 60 is removed, the gamma camera is unfolded 74 to convert it from the shipping configuration to the operational configuration. Optionally, the gamma camera 10 in the operational configuration at the destination site 66 is again tested 76 before being used for clinical, research, or other applications. In some embodiments, testing, alignment, or calibration at the destination can be omitted, instead relying upon the accuracy of the testing, alignment, or calibration at the factory or other manufacturing site 52 coupled with the use of the folding to retain the tested, aligned, or calibrated configuration during shipment.

Figure 8:
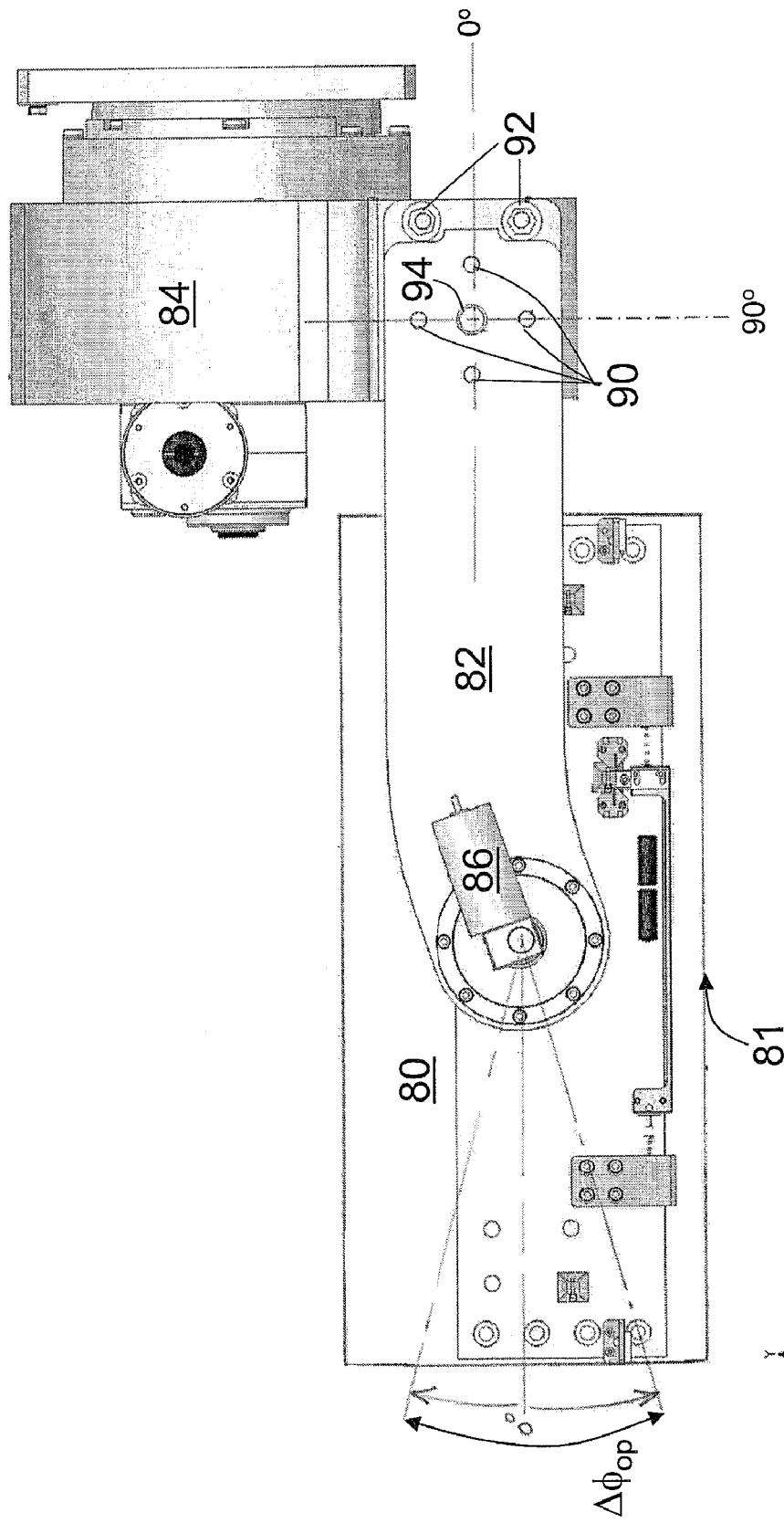
FIG. 8 shows an illustrative arrangement for reconfiguration of a detector head between operational and shipping configurations.

With reference to FIG. 8, an example of one illustrative detector head folding mechanism is described. A detector head 80 having a radiation-sensitive face 81 is mounted via an arm 82 to a detector-rotate housing or assembly 84. An automated tilt actuator 86 provides an operational, robotically driven tilt degree of freedom over an operative tilt angular range $\Delta\phi_{op}$. In this embodiment, the operational tilt degree of freedom is not optimal for folding, at least because it would leave the arm 82 sticking out from the gantry. Additionally, in some embodiments the operational tilt degree of freedom may provide less than a 90° tilt capability. Accordingly, an additional degree of freedom is provided for folding the detector head 80 as follows. In the operational configuration, the arm 82 is locked into position respective to the detector-rotate housing 84 by four fasteners 90 and two fine-adjust eccentrics 92. To place the gamma camera into the folded or shipping configuration, the fasteners 90 and eccentrics 92 are removed, and the detector head 80 is manually pivoted or rotated about a shoulder bolt 94 from the 0° operational position shown in FIG. 8 to a folded position in which the arm 82 is generally along the 90° orientation indicated in FIG. 2, with the radiation-sensitive face 81 facing the gantry. In some embodiments, the arm 82 may be pivoted less than 90°. In some embodiments, the arm 82 may be pivoted more than 90° as permitted by the frame 20, and may be moved partially into the bore of the frame 20 to further reduce the width. One or more of the fasteners 90 or eccentrics 92 is optionally reinstalled to lock the detector head 80 in the folded position during shipment, and to reduce a likelihood that the fasteners 90 or eccentrics 92 may be lost during shipment.

With reference to FIG. 9, an example of another illustrative detector head folding mechanism is described. A detector head 100 having a radiation-sensitive face 101 is rigidly mounted to an arm 102 via fasteners 103, and the arm 102 is in turn mounted to a detector-rotate housing or assembly 104 by a tilt or pivot connection 105. An automated tilt actuator 106 provides a robotically driven operational tilt degree of freedom about the tilt or pivot joint 105, but only over an operative tilt angular range $\Delta\phi_{op}$ that is substantially less than a full ±90°. To fold the detector head 100 against the gantry, one or both of the bolts or other fasteners 110, 112 are removed to remove the tilt actuator 106 completely or partially. With the tilt actuator 106 removed, the detector head 100 and rigidly connected arm 102 are free to pivot about the tilt or pivot joint 105 down to the indicated 90° position for shipping. In other words, by removing the fasteners 110, 112 and the robotic tilt actuator 106, the pivot joint 105 is converted from an operational degree of freedom spanning a limited angular interval $\Delta\phi_{op}$ into an additional degree of freedom allowing the detector head 100 and associated arm 102 to be rotated or folded into the shipping configuration.

The folding mechanisms of FIGS. 8 and 9 are suitable for incorporation into the frame 20 and actuators 22, 24 of the gamma camera 10 of FIGS. 1-6 to fold the respective detector heads 12, 14 generally toward the frame 20 to reduce protrusion of the detector heads away from the frame. In such a substitution, the detector head 80 or detector head 100 and associated mechanical components of respective FIG. 8 or 9 replace the one or both detector heads 10, 12 and selected components of the actuators 22, 24. Moreover, based on these illustrative examples, the skilled artisan can readily design other mechanical structures suitable for folding the detector heads of other gamma cameras generally toward the frame to reduce protrusion of the detector heads.

With reference to FIGS. 10-15, another embodiment is described. An imaging system 200 is similar to the gamma camera 10, but additionally includes an x-ray system comprising a radiation source, such as an x-ray tube 200, and a radiation detector, such as an x-ray detector array 202, mounted on the gantry 20 via respective arms 204, 206 along with the detector heads 12, 14 that are used for SPECT, PET, or the like. The x-ray tube 200 emits x-rays that pass through the examination region 30, and are attenuated by a subject disposed therein. The attenuated x-rays are detected by the x-ray detector array 202. Accordingly, the x-ray detector array 202 is a detector head; however, because collimation is provided by the x-ray tube 200-to-detector element path, the x-ray detector array 202 typically does not include a collimator, although it may include an anti-scatter grid or other receive angle-limiting structures. Moreover, the x-ray detector array 202 differs from the detector heads 12, 14 in other ways, such as being designed to receive a substantially higher flux of x-rays as compared with the low-level radiation typically detected by the detector heads 12, 14. Typically, the detector heads 12, 14 operate in a photon or particle counting mode in which each gamma ray, alpha or beta particle, or other radiation particle produces a discrete corresponding pulse of electrical current or other signal when it interacts with the radiation-sensitive face 16, 18 of the detector head 12, 14. The x-ray detector array 202 may operate in either a counting mode or in a continuous mode, the latter producing an electrical current or other signal whose intensity or amount is indicative of a level of substantially continuous x-ray flux impinging on the detector element.

The x-ray system 200, 202 can be used in a static mode, in which the azimuthal position of the x-ray tube 200 and the x-ray detector array 202 are held fixed, so as to acquire a planar x-ray image, such as a planar chest x-ray. Additionally or alternatively, the x-ray system 200, 202 can be used in a tomographic node, in which the azimuthal position of the x-ray tube 200 and the x-ray detector array 202 are incremented synchronously, so as to acquire tomographic projection data over a range of azimuthal angles that can be reconstructed into a slice or three-dimensional image representation. In some embodiments, the x-ray system 200, 202 is used acquire information about the subject from which an attenuation map is derived that is used to correct or adjust SPECT or PET imaging data or reconstructed images acquired by the detector heads 12, 14. In some embodiments, the x-ray system 200, 202 is used as an additional, complementary imaging modality along with SPECT and/or PET imaging provided by the detector heads 12, 14.

FIGS. 10, 11, and 12 show front, side, and top views, respectively, of the imaging system 190 in its operational configuration. The gamma camera components, such as the detector heads 12, 14, manipulators 22, 24 for manipulating the respective detector heads 12, 14, and so forth, are identical with those of the gamma camera 10 and accordingly are labeled with the same reference numbers as are used in FIGS. 1-3. The imaging system 190 additionally includes the x-ray tube 200 mounted on the arm 204 with the arm 204 extending generally away from the frame 20. Similarly, the x-ray detector array 202 is mounted on the arm 206 with the arm 206 extending generally away from the frame 20. In the operative configuration, the x-ray tube 200 and the x-ray detector array 202 are disposed in mutually facing fashion on opposite sides of the examination region 30. The x-rays generated by the x-ray tube 200 pass through the examination region 30 where they are attenuated based on the (generally spatially varying) x-ray absorption characteristics of the subject, and the x-ray detector array 202 on the opposite side receives and measures the intensity of the generally absorption-attenuated x-rays that pass through the examination region 30.

In the illustrated imaging system 190, the size $d_{op}$ of the imaging system 190 along the direction in which the detector heads 12, 14 protrude is limited by the extension of the detector heads 12, 14, with the x-ray system components 200, 202 extending or protruding a shorter distance in that direction. However, in other embodiments, the protrusion of the x-ray system components may be limiting. Even in the illustrated embodiment, however, the protrusion of the x-ray system components 200, 202 is large enough to prevent the operationally configured imaging system 190 from passing through hospital doorways, such as typically 40-inch wide doorways in the United States, 36-inch (90 cm) wide doorways in Europe, or both.

FIGS. 13, 14, and 15 show front, side, and top views, respectively, of the imaging system 190 in the folded or shipping configuration 190'. The detector heads 12, 14 are in the same folded positions as illustrated in FIGS. 4, 5, and 6 for the gamma camera 10. Additionally, the x-ray components 200, 202 are folded close to the frame 20. In the folded configuration 190', the x-ray tube 200 is rotated generally upward about a pivot joint 210, and optionally a length of the manipulator 204 is shortened via a telescopic mechanism, sliding-sleeve joint 212, or other suitable coupling. Similarly, in the folded configuration 190', the x-ray detector array 202 is rotated generally upward about a pivot joint 220, and optionally a length of the manipulator 206 is shortened via a telescopic mechanism, sliding-sleeve joint 222, or other suitable coupling. The imaging system 190 in the shipping configuration 190' is suitably packaged, for example with packaging material 160 as shown diagrammatically in phantom in FIGS. 13-15, and shipped in accordance with the method diagrammatically shown in FIG. 7.

While in the illustrated embodiment the x-ray components 200, 202 remain mechanically attached to the frame 20 during shipping, in other embodiments it is contemplated to remove one or both of the x-ray components prior to shipping and to re-install these components at the destination site.

The illustrative embodiments are examples, and numerous variations are contemplated for enabling configuration of an imaging system in a shipping configuration in which the detector heads remain at least mechanically attached with the gantry. In the illustrated embodiments, the operational degrees of freedom of the gantry are inadequate to enable a folded or shipping configuration of sufficiently small size; accordingly, additional degrees of freedom such as the tilt or pivot joints 41, 42, the translational mechanisms 43, 44, and the pivot joints 210, 220 are provided. In the illustrated embodiments, the additional degrees of freedom are manually actuated; however, it is also contemplated to incorporate suitable robotic actuators into the gantry so as to operate these additional degrees of freedom in an automated or semi-automated fashion. If the operational degrees of freedom are sufficient to place the imaging system into a sufficiently compact folded configuration, then it is contemplated to omit the additional degrees of freedom and to ship the imaging system with the detector heads at least mechanically attached but in the compact folded configuration achieved using only operational degrees of freedom.

In the illustrated embodiments, at least some additional degrees of freedom 41, 42, 210, 220 are provided for the folding, and are locked into fixed positions when the frame is in the operational configuration. In some embodiments, the locked fixed position may be used as an alignment or calibration mechanism. For example, the four fasteners 90 and two fine-adjust eccentrics 92 of the folding mechanism of FIG. 8 lock the arm 82 into a fixed position that is fine tuned using the eccentrics 92 to align or calibrate the tilt of the detector head 80 respective to the pivot joint 94.

In the illustrated embodiments, placement of the imaging system 10, 190 into the folded or shipping configuration involves additional degrees of freedom actuated along with or in cooperation with some operational degrees of freedom. For example, the detector-rotate mechanisms 32, 34 which provide rotational operational degrees of freedom for the respective detector heads 12, 14 are also used in the folding process. Similarly, the sliding-sleeve joints 212, 222 are suitably used both to provide operational degrees of freedom for the respective x-ray components 200, 202 (for example, to position these components at a selected distance from the frame 20 for x-ray imaging) and are also optionally used during the folding process to shorten the arms 204, 206. However, it is also contemplated to use only dedicated additional degrees of freedom and not any operational degrees of freedom in the folding process. On the other hand, if the operational degrees of freedom are sufficiently flexible, it is contemplated to place the imaging system into the folded or shipping configuration using only the operational degrees of freedom, in which case no additional degrees of freedom are provided.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An imaging system comprising:
    a gamma camera including a plurality of detector heads and a frame on which the plurality of detector heads are mounted,
    wherein the frame is configurable in (i) an operational configuration in which the detector heads are arranged to be manipulated by the frame to acquire imaging data, and (ii) a shipping configuration in which the detector heads remain mounted on the frame and the imaging system is reduced in size along at least one dimension compared with the operational configuration, and
    wherein the frame has at least one mechanical degree of freedom that is used in switching between the operational configuration and the shipping configuration and that is locked into a fixed position when the frame is in the operational configuration.

2. The imaging system as set forth in claim 1, wherein the at least one mechanical degree of freedom that is used in switching between the operational configuration and the shipping configuration is manually operated to place the imaging system in the shipping configuration.

3. The imaging system as set forth in claim 1, wherein the frame has at least one pivoting degree of freedom that is used to tilt a detector head between an extended position extending generally away from the frame and a folded position relatively closer to the frame.

4. The imaging system as set forth in claim 1, wherein the detector heads remain electrically connected with the frame in the shipping configuration.

5. The imaging system as set forth in claim 1, wherein the shipping configuration is reduced to a size less than 40 inches along at least one dimension.

6. The imaging system as set forth in claim 1, wherein the shipping configuration is reduced to a size less than 36 inches along at least one dimension.

7. A shipping package comprising:
    the imaging system as set forth in claim 1 configured in the shipping configuration in which the detector heads remain mounted on the frame; and
    packaging material containing or covering at least a portion of the imaging system.

8. The imaging system as set forth in claim 1, further comprising:
    an x-ray system including an x-ray tube mounted on the frame of the gamma camera and an x-ray detector mounted on the frame of the gamma camera.

9. An imaging system comprising:
    a plurality of detector heads;
    a frame; and
    manipulators mechanically and electrically connecting the detector heads with the frame, the manipulators including a plurality of operational degrees of mechanical freedom usable in operating the imaging system to acquire imaging data and at least one additional degree of mechanical freedom that is not used in operating the imaging system, the at least one additional degree of mechanical freedom being usable to selectively arrange the imaging system in a shipping configuration in which the plurality of detector heads are mechanically connected with the frame and the imaging system has a reduced size in at least one dimension compared with a size of the imaging system during imaging data acquisition.

10. The imaging system as set forth in claim 9, wherein the plurality of detector heads are electrically connected with the frame in the shipping configuration.

11. The imaging system as set forth in claim 9, wherein the at least one additional degree of mechanical freedom includes a pivot enabling the connected detector head to be tilted to a position in which a radiation-sensitive face of the detector is relatively more parallel with a principal plane of the frame compared with an operational position of the connected detector head.

12. The imaging system as set forth in claim 9, wherein the at least one additional degree of mechanical freedom includes at least one degree of mechanical freedom that is operable upon removal of one or more locking fasteners to arrange the imaging system in the shipping configuration.

13. The imaging system as set forth in claim 9, wherein the at least one additional degree of mechanical freedom includes a pivot operable upon removal of one or more locking fasteners to tilt the detector head generally toward the frame to reduce a protrusion of the detector head away from the frame.

14. The imaging systems set forth in claim 9, wherein the at least one additional degree of mechanical freedom cooperates with one or more operational degrees of mechanical freedom to arrange the imaging system in the shipping configuration.

15. A delivery method for delivering an imaging system, the method comprising:
providing an imaging system as set forth in claim 9 at a first location by operations including:
at the first location, mounting the plurality of detector heads on the frame via the manipulators,
at the first location, electrically connecting the detector heads with the frame, and
at the first location, placing the imaging system into the shipping configuration using the at least one additional degree of mechanical freedom; and
shipping the imaging system in the shipping configuration from the first location to a second location different from the first location.

16. The delivery method as set forth in claim 15, further including:
testing the imaging system at the first location to verify the mounting and electrical connecting.

17. The delivery method as set forth in claim 15, wherein the shipping includes:
passing the imaging system in the shipping configuration through a doorway having a width of 40-inches or less.

18. The delivery method as set forth in claim 15, wherein the plurality of detector heads remain electrically connected with the frame during the shipping.

19. The delivery method as set forth in claim 15, wherein the placing of the detector heads in the shipping configuration includes:
folding at least one detector head relatively toward the frame using the at least one additional degree of mechanical freedom.

20. The delivery method as set forth in claim 15, wherein the placing of the imaging system into the shipping configuration includes:
pivoting at least one detector head about a pivot joint toward the frame using the at least one additional degree of mechanical freedom.

21. A shipping package comprising:
the imaging system as set forth in claim 9 configured in the shipping configuration; and
packaging material containing or covering at least a portion of the imaging system.

22. The shipping package as set forth in claim 21, wherein the plurality of detector heads are electrically connected with the frame.

23. An imaging system comprising:
a plurality of detector heads;
a frame;
manipulators mechanically and electrically connecting the detector heads with the frame, the manipulators including a plurality of operational degrees of mechanical freedom usable in operating the imaging system to acquire imaging data and at least one additional degree of mechanical freedom usable to selectively arrange the imaging system in a shipping configuration in which the plurality of detector heads are mechanically connected with the frame and the imaging system has a reduced size in at least one dimension compared with a size of the imaging system during imaging data acquisition;
wherein the at least one additional degree of mechanical freedom includes a pivot operable upon removal of one or more locking fasteners to tilt the detector head generally toward the frame to reduce a protrusion of the detector head away from the frame and further includes a translational mechanism configured to translate at least one detector head along the frame.

24. An imaging system comprising:
a plurality of detector heads;
a frame;
manipulators mechanically and electrically connecting the detector heads with the frame, the manipulators including a plurality of operational degrees of mechanical freedom usable in operating the imaging system to acquire imaging data and at least one additional degree of mechanical freedom usable to selectively arrange the imaging system in a shipping configuration in which the plurality of detector heads are mechanically connected with the frame and the imaging system has a reduced size in at least one dimension compared with a size of the imaging system during imaging data acquisition;
an x-ray detector array configured for use in computed tomography (CT) imaging, at least one of the manipulators connecting the x-ray detector array with the frame;
an x-ray source configured for use in computed tomography (CT) imaging; and
a manipulator connecting the x-ray source with the frame;
wherein at least one of the x-ray detector array and the x-ray source remains at least mechanically connected with the frame in the shipping configuration.

25. An imaging system comprising:
a gamma camera including a plurality of detector heads, a frame, and manipulators mechanically and electrically connecting the detector heads with the frame;
wherein the manipulators have a plurality of operational degrees of mechanical freedom usable in operating the gamma camera to acquire imaging data;
wherein the manipulators have at least one additional degree of mechanical freedom that is not usable in operating the gamma camera to acquire imaging data and that is usable to place the gamma camera into a shipping configuration in which the plurality of detector heads are mechanically connected with the frame and the gamma camera has a reduced size in at least one dimension compared with a size of the gamma camera during imaging data acquisition.

26. An imaging system comprising:
a gamma camera including a plurality of detector heads, a frame, and manipulators mechanically and electrically connecting the detector heads with the frame; and
an x-ray system including an x-ray tube mounted on the frame of the gamma camera and an x-ray detector mounted on the frame of the gamma camera;
wherein the manipulators have a plurality of operational degrees of mechanical freedom usable in operating the gamma camera to acquire imaging data;
wherein the manipulators have at least one additional degree of mechanical freedom that is not usable in operating the gamma camera to acquire imaging data and that is usable to place the gamma camera into a shipping configuration in which the plurality of detector heads are mechanically connected with the frame and the gamma camera has a reduced size in at least one dimension compared with a size of the gamma camera during imaging data acquisition.

27. The imaging system of claim 26, wherein at least one of the x-ray tube and the x-ray detector array remains mechanically connected with the frame of the gamma camera when the gamma camera is in the shipping configuration.

* * * * *